United States Patent
Morsey

(10) Patent No.: US 9,381,000 B2
(45) Date of Patent: Jul. 5, 2016

(54) DEVICES AND METHODS FOR THE DETECTION OF STREP A

(71) Applicant: Kathleen Morsey, Rowayton, CT (US)

(72) Inventor: Kathleen Morsey, Rowayton, CT (US)

( * ) Notice: Subject to any disclaimer, the term of this patent is extended or adjusted under 35 U.S.C. 154(b) by 0 days.

(21) Appl. No.: 14/216,424

(22) Filed: Mar. 17, 2014

(65) Prior Publication Data

US 2014/0315221 A1 Oct. 23, 2014

Related U.S. Application Data

(60) Provisional application No. 61/802,059, filed on Mar. 15, 2013, provisional application No. 61/811,023, filed on Apr. 11, 2013, provisional application No. 61/827,994, filed on May 28, 2013.

(51) Int. Cl.
*G01N 33/569* (2006.01)
*A61B 10/00* (2006.01)

(52) U.S. Cl.
CPC ...... *A61B 10/0051* (2013.01); *G01N 33/56944* (2013.01)

(58) Field of Classification Search
None
See application file for complete search history.

(56) References Cited

U.S. PATENT DOCUMENTS

| | | |
|---|---|---|
| 4,826,227 A | 5/1989 | Lew |
| 2004/0220498 A1 | 11/2004 | Li |
| 2009/0306543 A1 | 12/2009 | Slowey et al. |

OTHER PUBLICATIONS

Ryan "Rock Candy Lollipops Recipe" The Spinning Cook, Good Food for Fast Families Posted on Mar. 9, 2013, http://spinningcook.com/2013/rock-candy-lollipops-recipe/.
Bisno, Group A Streptococcal Infections and Acute Rheumatic Fever. The New England Journal of Medicine, 325:783-793, Sep. 12, 1991.
Kuttner et al., Observations on the effect of streptococcal upper respiratory infections on rheumatic children: a Three-Year Study. Clin. Invest.:273-287, 1941.
Shea, Specimen Collection and Transport, Clinical Microbiology Handbook; Aerobic Bacteriology; Am Society of Mirobiology: 1.1 1-11.30, 1992.
Polymedcro Inc., Poly Stat Strep A Strip Test leaflet.
CDC Website, GAS Frequently Asked Questions—group A Streptococcus, 2011. <http://www.cdc.gov/groupastrep/about/faqs.html>.
UCSF Medical Center Clinical Laboratories, Point of Care Testing, approved by T. Hamil, MD, date unavailable.
Seeking Alpha, Quidel Corporation's CEO Presents at the JP Morgan Healthcare Conference (Transcript), Jan. 11, 2012.
Smith, R.: The Spinning Cook, Good Food for Fast Families: Rock Candy Recipe, p. 1, image 1; p. 2, image 2; image 1, lines 18-24, 30; p. 3, lines 16-22, Mar. 9, 2013. <http://spinningcook.com/2013/rock-candy-lollipops-recipe>.
International Search and Written Opinion issued in related international application No. PCT/US2014/030638, mailed Nov. 7, 2014.
Fitzpatrick, J.; Lifehacker: Use A Ruber Band to Turn Disposable Chopsticks Into A Training Set, third paragraph; May 14, 2012. <https://web.archive.org/web/20120514053635/http://lifehacker.com/5616695/use-a-rubber-band-to-turn-disposable-chopsticks-into-a-training-set>.

*Primary Examiner* — J. Hines
*Assistant Examiner* — Khatol Shahnan Shah
(74) *Attorney, Agent, or Firm* — Day Pitney LLP

(57) ABSTRACT

The present disclosure relates to devices and methods for rapidly detecting streptococcus bacteria. An illustrative device includes a first elongate handle connected to a first edible portion and a second elongate handle connected to a second edible portion. The first and second elongate handles are connected by a banding material. The first and second edible portions are inserted into the mouth of an individual for receiving a saliva sample.

10 Claims, 6 Drawing Sheets

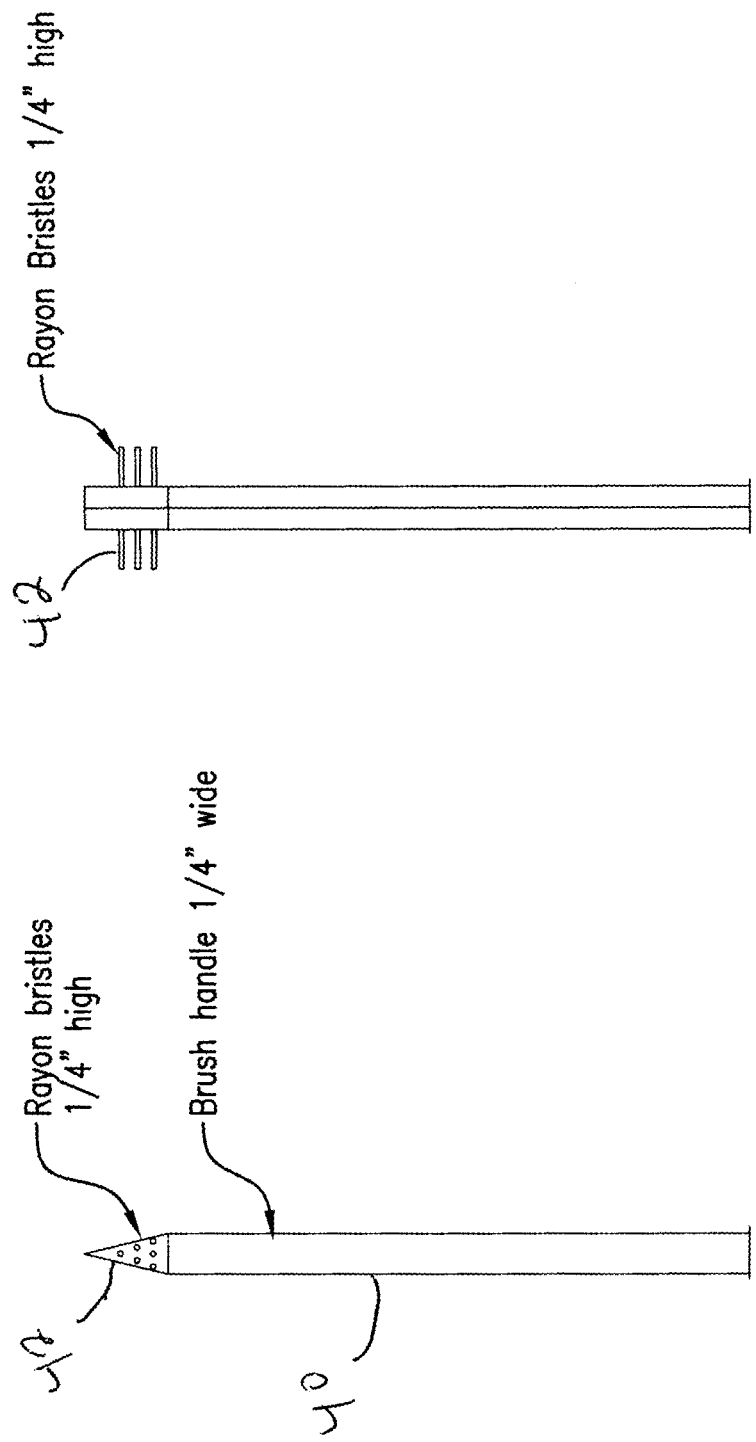

DEVICES AND METHODS FOR THE DETECTION OF STREP A

CROSS-REFERENCE TO RELATED APPLICATIONS

This application claims priority to U.S. Patent Provisional Application 61/802,059, filed on Mar. 15, 2013, U.S. Patent Provisional Application No. 61/811,023 filed on Apr. 11, 2013 and U.S. Patent Provisional Application No. 61/827,994 filed May 28, 2013, the disclosures of which are incorporated herein by reference in their entirety for any purpose whatsoever.

BACKGROUND

1. Field

The present application relates to medical devices and methods for the detection of the Streptococcus bacteria.

2. Description of Related Art

According to the CDC, there are several million cases of Group A-hemolytic streptococcus bacterial infection (Strep A) reported each year. The strep bacteria is transmitted through the air and is highly contagious. Children who contract strep throat can develop PANDAS (Pediatric Autoimmune Neuropsychiatric Disorders), a disorder associated with streptococcal infections. One of the symptoms of PANDAS is OCD (Obsessive Compulsive Disorder). For years medical experts thought the link between a strep throat and OCD was only coincidental, but now many believe PANDAS affects the part of the brain that controls movement and behavior. CDC guidelines for medical doctors state that a strep test should be performed if a patient presents with two of the four symptoms, namely: white matter on tonsils; fever; painful swollen glands; and a lack of coughing. Group A Streptococcus is one of the most significant human pathogens causing acute pharyngitis, tonsillitis impetigo, and scarlet fever. It is very important to differentiate streptococcal infection from other etiologic agents so that appropriate therapy may be initiated. Rapid diagnosis and timely treatment of Group A Streptococcal pharyngitis infections will reduce the severity of symptoms and further complications such as rheumatic fever and glomerulonephritis.

The accurate diagnosis of Strep A in children is largely dependent on the cooperation of the child and the medical practitioner's ability to collect a good specimen. The current device for collecting a sample is a sterile swab comprised of polyester and rayon. The tip rests at the end of a wooden stick which measures six inches in length. The method of specimen collection involves the use of two sterile swabs held together and simultaneously inserted into a child's mouth. In children over the age of 6, the child's head is tipped slightly backward so that the practitioner can visualize the tonsils. The tonsils are then swabbed with the sterile swabs. This sensation for many children is uncomfortable and engages the gag reflex. For children undergoing the conventional swab method, it often feels as if the swabs are being jammed or forced down their throat. In children ages 2-5, the practitioner must hold the child's jaw firmly with one hand while trying to swab the throat with the other. Parents are often asked to assist in mildly restraining their children so that the swabs may be inserted far enough into the mouth in order to reach the back of the throat to collect the specimen. This method is unpleasant for the child and awkward to administer for the practitioner. However, this is the only test on the market for the diagnosis of Strep A bacteria. One swab is used for the rapid test, performed on site in the practitioner's office or on-site laboratory, and the other swab is sent to an off-site lab to be cultured. With a rapid strep test, results are ready in 10 minutes instead of 1 to 2 days with a throat culture. The rapid test utilizes a chromatographic immunoassay for the qualitative detection of Group A Streptococcal antigen. Test strips or devices are treated with specific Strep A antibodies which react with the Strep A antigen if the bacteria is present. If the rapid strep test results are positive, antibiotics may be started immediately. The rapid strep test can give false-negative results even when strep bacteria are present. For these reasons, a throat culture is more accurate than the rapid strep test. Regardless, the accuracy of these tests is totally dependent on the collection of a good sample from the mucosa located in the back of the throat where the Strep A bacteria cultivates. The present application advances the current method and eliminates the problem of unpleasantness for a child and awkwardness for the medical practitioner while ensuring a sufficient sample is obtained.

SUMMARY

Advantages of the present disclosure will be set forth in and become apparent from the description that follows. Additional advantages of the disclosure will be realized and attained by the methods and systems particularly pointed out in the written description and claims hereof, as well as from the appended drawings.

The present disclosure relates to devices and related methods for rapidly detecting streptococcus bacteria. One embodiment of a device includes a first elongate handle having a proximal end and a distal end, the distal end of the first handle being connected to a first edible substance, a second elongate handle having a proximal end and a distal end, the distal end of the second handle being connected to a second edible substance. The first elongate handle is connected to the second elongate handle by a banding material. The first edible substance and the second edible substance are configured to be inserted into the mouth of an individual for receiving a saliva sample.

In some embodiments, the first and second edible substances can include a plurality of edible components selected from the group consisting of corn syrup, sugar, water, gelatin, modified corn syrup, and mineral oil. the first and second edible substances can include flavored material. The first and second elongate handles can include at least one of plastic and wood, among other materials. The banding material can include glue, tape, paper, or any other suitable material.

The disclosure also provides an illustrative device for rapidly detecting streptococcus bacteria. The device includes an outer elongate tubular handle having a proximal end and a distal end, the distal end of the outer elongate tubular handle being disposed within an edible substance. The device further includes a plurality of swabs for receiving a saliva sample slidably disposed within an elongate passage of the outer elongate tubular handle.

If desired, the device can further include an elongate proximal handle disposed within the elongate passage of the outer elongate tubular handle. The elongate proximal handle can be disposed in operable communication with the plurality of swabs to advance the plurality of swabs into a throat of a patient after the edible material is disposed in the mouth of the patient.

The disclosure further provides a device for rapidly detecting streptococcus bacteria, including an outer elongate tubular handle having a proximal end and a distal end, and a plurality of swabs slidably disposed within the outer elongate flavored tubular handle, each swab being mounted on a respective elongate member.

The device can further include an elongate proximal handle disposed within the elongate passage of the outer elongate tubular handle, the elongate proximal handle being disposed in operable communication with the plurality of swabs to advance the plurality of swabs into a throat of a patient after the edible material is disposed in the mouth of the patient. If desired, the outer elongate tubular handle includes edible flavored material.

The disclosure further provides a method for rapidly detecting streptococcus bacteria, comprising inserting a first elongate handle connected to a first edible substance and a second elongate handle connected to a second edible substance into the mouth of an individual for a predetermined amount of time until saliva is received on the first and second edible substances, removing a banding material that connects the first elongate handle from the second elongate handle, and testing the first and second edible substances for strep A bacteria. Similar methods may be practiced with any embodiment disclosed herein.

The disclosure further provides a further device for the rapid detection of strep A including a plurality of elongate handles attached by a banding material, each elongate handle including a row of bristles located at the distal end of the elongate handles including edible material, the bristles being configured to receive a saliva sample from a patient. If desired, the bristles can include a strep A antigen.

The disclosure still further provides a device for the rapid detection of streptococcus bacteria, including a first elongate handle connected to a first edible substance having a plurality of bristles suitable for receiving a saliva sample from a patient, and a second elongate handle connected to a second edible substance having a plurality of bristles suitable for receiving a saliva sample from a patient. The first and second elongate handles can include, for example, at least one of plastic and wood. The banding material can include, for example, glue or tape.

The disclosure yet further provides a device for the rapid detection of streptococcus bacteria, including a first component for disposing in the mouth of a patient, the first component including a an inner hollow channel, the inner hollow channel ending in a test tube that is connected to the base of the mouthpiece, the test tube being configured to receive a saliva sample when the patient coughs into the first component. In another embodiment, a device for the rapid detection of streptococcus bacteria, includes a piece for fitting into the mouth of an individual. The mouthpiece includes an inner hollow channel located at the base of the mouthpiece distal into the mouth of the individual. The inner hollow channel culminates into a test tube which is connected to the base of the mouthpiece. The test tube is used for the receiving of a saliva sample by the individual coughing into the mouthpiece.

It is to be understood that the foregoing general description and the following detailed description are exemplary and are intended to provide further explanation of the disclosed embodiments. The accompanying drawings, which are incorporated in and constitute part of this specification, are included to illustrate and provide a further understanding of the disclosed methods and systems. Together with the description, the drawings serve to explain principles of the disclosure.

BRIEF DESCRIPTION OF THE DRAWINGS

FIG. 4A is a schematic illustration of an alternative embodiment of a device for the detection of Strep A.

FIG. 4B is a side view of the alternate embodiment of a device for the detection of Strep A shown in FIG. 4A.

DETAILED DESCRIPTION

The present application relates to diagnostic tests, particularly for the pediatric population for the detection of Strep A bacteria, a test that is more user friendly compared to the current polyester swab method. The preferred embodiment of the application replaces the conventional sterile swab with, for example, a gelatin-based circular/rounded substance (a "lollipop-like" or candy-like object) on a stick for a child-friendly diagnostic test for Strep A. As a lollipop, for example, children of all ages are familiar with the shape and therefore less fearful of the gag reflex they have come to expect from conventional sterile swabs. Since lollipops are "treats" for children, the circular/rounded shape triggers a pleasant and fun feeling for the child. Sucking on lollipops is instinctive for children and is done independently while still under the supervision of the practitioner. Applicant intends that the name of the device will be branded and marketed as StrepPop™.

Figure 1:
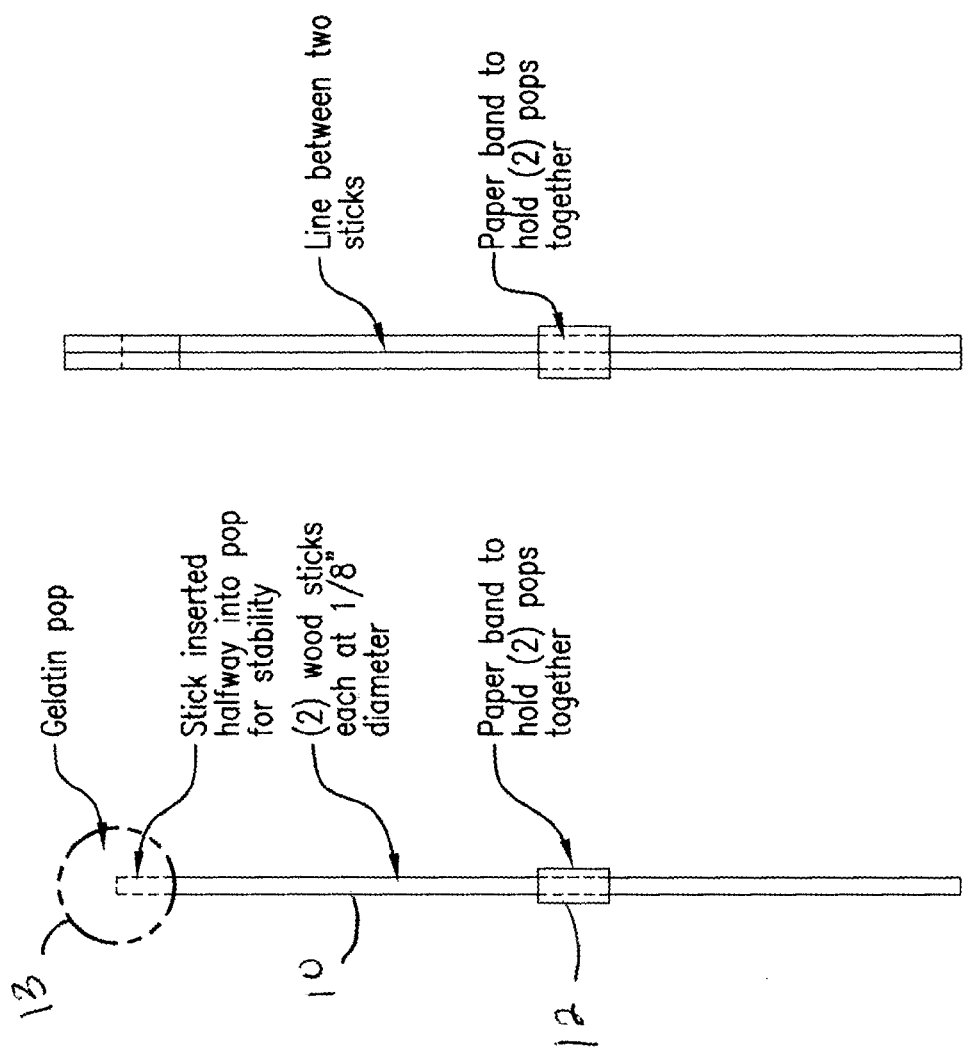
FIG. 1A is a schematic illustration of a device for the detection of Strep A.
FIG. 1B is a side view of the device for the detection of Strep A shown in FIG. 1A.

In FIG. 1, an illustrative device includes a circular, organic, soft, gelatinous substance 13 preferably measuring, for example, $13/16"$ wide and $2/16"$ in depth. The substance 13 of the circular member may include corn syrup, sugar, water, gelatin, modified corn syrup, mineral oil, and the like. The substance of the circular member 13 may be clear in color and non-flavored. The circular substance 13 is attached to the distal end of a wooden stick handle 10 which measures 6" long. The stick, as illustrated, is rounded and has a diameter of $2/16^{th}$ of an inch. The stick 10 is inserted into the circular substance, for example, at a midway point 14, approximately $71/16^{th"}$ deep in order to secure the circular member onto the stick, such as by the adhesive properties of the substance of the circular member. An identical circular member, on an identical stick, is banded with another circular member on the stick device. The two devices are banded together, for example, $21/2"$ from the bottom of each device (second device not shown) The banding material 12 is a paper or other wrap which is glued and is $1/2"$ thick. An intact band signifies that the device is sterile. The paper band remains intact until after the specimen has been collected. The band is cut or broken by the practitioner after removal from the patient's mouth and one device is used for the rapid test, and the other device is sent away to be cultured. The device's circular, lollipop-like component may further include any material that is best identified for sample and specimen collection, including but not limited to, rayon polyester, cotton or any safe or nontoxic material suitable for this purpose. In another embodiment, the banding material may be made of any material which can secure the handle and be easily breakable. In another embodiment, the handle may be flat or may be of a plastic material. It will be appreciated by those of skill in the art that reference to dimensions herein of the disclosed embodiments are meant only as examples, and that the precise dimensions disclosed are not critical.

In another embodiment, the device may be in the classic lollipop shape or in more playful shapes such as different animals, fictional characters, cartoon characters or popular culture references known to children, or any other suitable shape. The device can also be available in varying sizes depending on the age of the child. In addition, the clear organic, soft, gelatinous substance of the device may be available in attractive, bright or neon colors. The device may be one solid color or arranged in multiple colors, stripes and polka dots. In another embodiment, the device may be available in different flavors, including but not limited to strawberry, cherry or grape, citrus, lemon, lime, orange, and the like.

Figure 2:
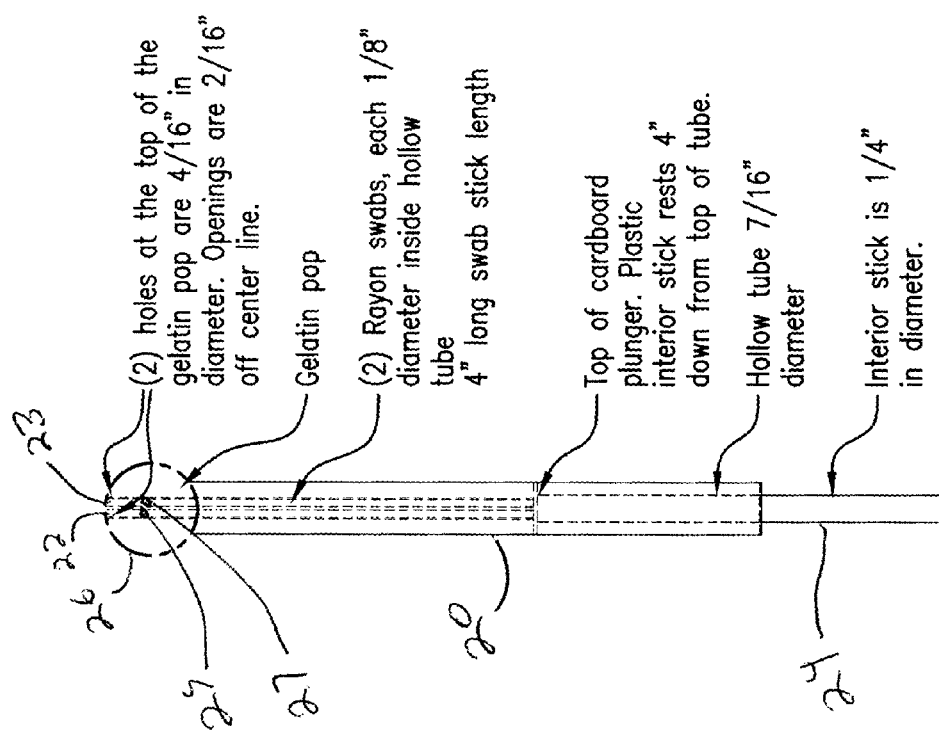
FIG. 2 is a schematic illustration of an alternative embodiment of a device for the detection of Strep A.

In FIG. 2, another illustrative embodiment of the application is illustrated. In this embodiment, the circular member 26 includes an organic, soft, gelatinous substance measuring 13/16" wide and 7/16" in depth. The substance of the circular member 26 includes corn syrup, sugar, water, gelatin, modified corn starch, and mineral oil. The substance is clear in color and non-flavored. The tube which holds the circular member is made of wood 20. The tube is 5¾" long and 7/16" in outer diameter. The tube 20 is rounded, hollow and may be made of any safe and nontoxic material such as unfinished solid wood, hemp or BPA-Free PVC-free plastic #2, #4, #5. The tube 20 is inserted all the way to the top edge of the circular member in order to secure the circular substance to the stick. The circular member contains two openings 22 and 23 close to the outer rim of the circular member, each opening measuring $4/16^{th}$" in diameter. Each opening 22 and 23 is placed $2/16^{th}$" off the center line. The center line is located 6 and one half sixteenths measured from the edge of the circular member. The tube 20 can accommodate an interior stick 24 which is comprised of plastic and is $4/16^{th}$" in diameter. The interior stick 24 is 4 inches long and rests 4" down from the top of the tube at the base of the rayon swabs. While the device is in the mouth of a child, the interior stick 24 is pushed forward, and the two polyester swabs 25 and 27 eject through the two holes on the top of the device 22 and 23. Subsequently, the two swabs 25 and 27 touch the tonsils at the back of the throat, and a specimen is collected. The swabs 25 and 27 are removed from the top of the pop and one swab is used for the rapid test, and the other is sent off site for the throat culture. The device is then discarded.

It will be appreciated that the embodiment of FIG. 2 can be varied in many ways. For example, it will be appreciated that the dimensions may be varied, as desired, and that the shape of the cross section of the tubular member may be circular, rectangular, elliptical, oval, triangular in shape or have any other suitable shape. It will further be appreciated that while the disclosed embodiment depicts two swabs being delivered, any desired number of swabs (e.g., three) can be delivered.

Figure 3:
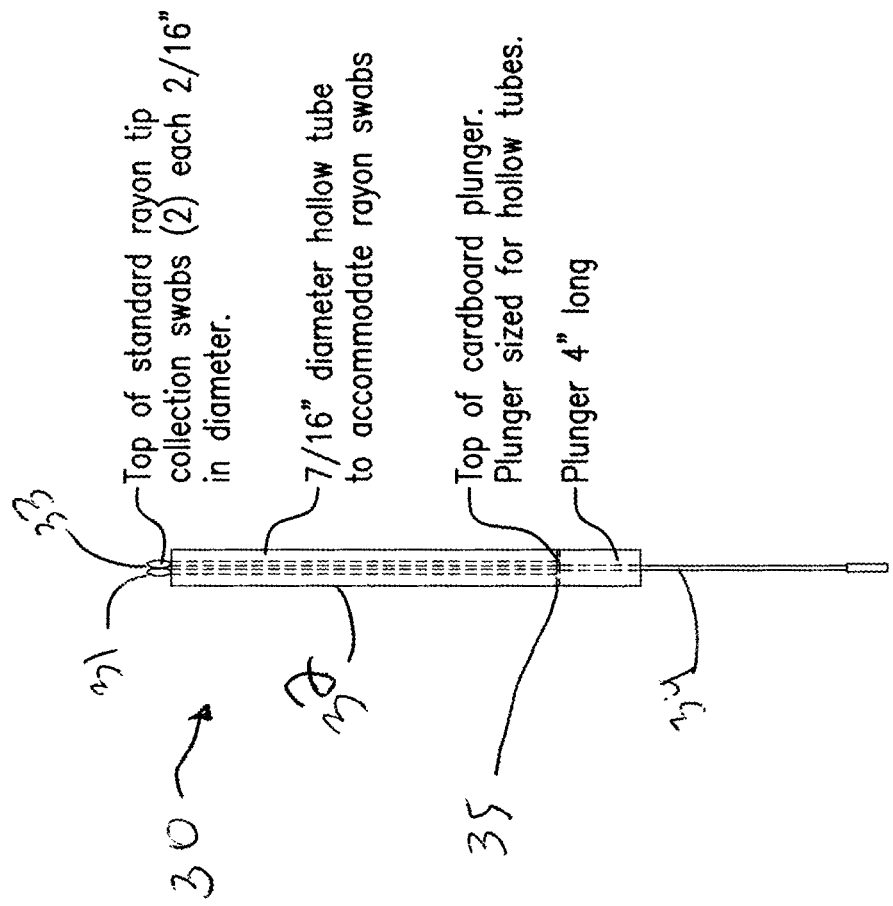
FIG. 3 is a schematic illustration an alternative embodiment of a device for the detection of Strep A.

In FIG. 3, an alternative embodiment of the device omits the "lollipop" feature. The disclosed device 30 accordingly contains a hollow tube 32 which, in the illustrated embodiment, measures $7/16^{th}$" in diameter and is 5¾" in length. The hollow tube 32 is made of plastic, but can be made from any suitable material. The hollow tube 32 contains two (e.g.,) rayon swabs 31 and 33 which are located at the distal end of the hollow tube 32. Each rayon swab 31 and 33 is $2/16^{th}$" in diameter. A solid cardboard cylinder 34 acts as a plunger. The solid cardboard cylinder 34 measures 4/16" in diameter and is 4" long. The cardboard cylinder 34 would push forward the rayon swabs. The outside of the hollow tube 32 would measure how far the swabs are pushed forward. A measurement line 35 on the hollow tube 32 would indicate that the cardboard has pushed the rayon swabs (31 and 33) 13/16" outward from the top of the vessel. This would be sufficient depth to touch the mucosa in the child's throat. The second position would eject the swabs 31 and 33 another two inches, such that the swabs may be safely removed by the practitioner. One swab would be used for the rapid test, and one swab would be sent for a throat culture. The hollow tube could be manufactured in a variety of flavors making the hollow tube more palatable for the child. Since the swabs are safely housed inside the hollow tube until pushed forward by the cardboard cylinder, the flavoring of the hollow tube would not come in contact with the specimen.

In FIG. 4, a further illustrative embodiment of a device includes a double-sided brush mechanism for use on the surface of a child's teeth. The device is comprised of a small colorful handle 40 which measures 4" long and made of plastic. The handle 40 of the brush is flat and $4/16^{th}$" wide. At the distal end of the handle are three rows of rayon bristles 42. From the first row of bristles to the third row of bristles, the bristles measure $4/16^{th}$" wide by 4/16" long by 8/16" in height. The bristles 42 form a triangle comprised of three rows of bristles. Each triangle set of bristles is configured as three bristles in one row, two bristles in the second and one bristle in the third row. Each set of bristles 42 is comprised of a cluster of rayon bristles packed together tightly. The bristles may be made of any material, such as polyester, cotton or microfiber. There are two of these brush mechanisms banded back-to-back (not shown). The brush mechanism could also be produced to include but not limited to, fun shapes, colors, and animal shapes. The band is broken only after the specimen has been collected. One brush's specimen is used for the rapid test, and the other brush's specimen is used for the overnight culture. While not shaped like a device, a proper specimen is able to be collected from the child by brushing the rayon swabs over the top and bottom teeth simultaneously. A child could do this alone or with support from the practitioner. Like sucking on a lollipop, brushing one's teeth is a familiar and pleasant task for a child. In another embodiment, colored bristles would be impregnated with Strep A antibodies. The child then brushes his teeth, mouth and/or tongue which causes the production of saliva. The saliva is collected on the bristles. The bristles would change to a different color if the Strep A antigen is detected in the saliva. In another embodiment, a similarly shaped test tube is impregnated with the Strep A antibodies When the brush device is inserted into the tube, the brush changes color when the Strep A antigen is present. In another embodiment, the test tube may contain a test trip which contains the Strep A antigen, such that when the bristles comes in contact with test strip, the test strip changes color to signify that the Strep A bacteria is present in the saliva sample.

The embodiments described in FIGS. 1, 2, and 3 are given to a patient to suck on for 60 seconds to ensure that it is well-coated with a potential streptococcus bacteria. The patient is instructed by the practitioner not to touch the device to the sides of the cheek. Instead, the patient would be instructed to touch the device to the tongue and top of the mouth area. After the 60-second period, the practitioner takes the device back to the testing area and removes the band that secures the two devices together. One device is placed in the rapid test vessel, which mirrors the shape of the device. At this point, either Reagent A, sodium nitrate, Reagent B, phosphoric acid, or acetic acid are placed in the device-shaped vessel to determine the presence of the Strep A antigen. The test strip is then inserted which shows a control line and a positive or negative result. The other device is sent to the laboratory to be cultured. All embodiments further the art in this field by creating a new diagnostic tool which is child-friendly and which assists in the accurate diagnosis of the Strep A bacteria.

Figure 5B:
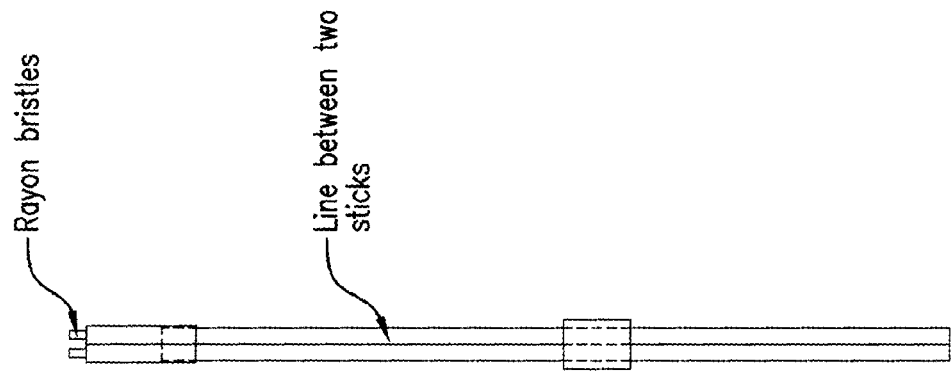
FIG. 5B is a side view of the alternate embodiment of a device for the detection of Strep A shown in FIG. 5A.
Figure 5A:
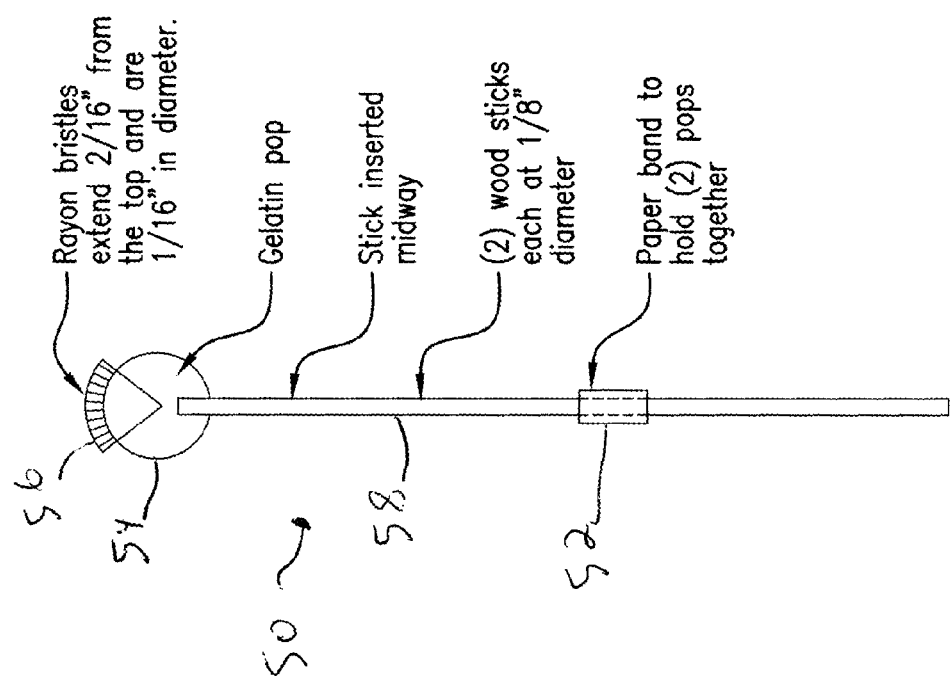
FIG. 5A is a schematic illustration of an alternative embodiment of a device for the detection of Strep A.

In FIG. 5, an alternative embodiment of the device 50 is comprised of a circular, organic, soft, gelatinous substance 54 which measures 13/16" wide and 4/16" in depth. The ingredients of the circular member substance 54 include corn syrup, sugar, water, gelatin, modified corn syrup, and mineral oil. The circular substance is soft and gelatinous in texture. The circular substance is clear in color and non-flavored. Spanning across the top of the arc of the circular member are rayon bristles 56 which protrude 2/16$^{th}$" from the circular member. The length of the span across the top of the arc of the circular member is 8/16$^{th}$". The rayon bristles run the length of the circular member and are imbedded into the circular member, such that the bristles are secure. The bristles may be made of any material, such as polyester, cotton or microfiber. The device circular lollipop component may be comprised of any material that is best identified for sample and specimen collection, including but not limited to, rayon or polyester, or any safe or nontoxic material suitable for this purpose. The rayon bristles 56 are 1/16$^{th}$" in diameter. The wooden stick measures 5¾" long. The wooden stick 58 is inserted into the circular substance midway to approximately 7½/16$^{th}$, such that the wooden stick 58 is secured to the circular member and forms a lollipop formation or device. The wooden stick 58 is comprised of solid wood and is 2/16$^{th}$" in diameter. An identical device with identical rayon bristles is paired with another service as described, and both are banded to each other (not shown). The identical devices are banded together at 2½" from the bottom of each. The banding material 52 is a paper wrap which is glued and is ½" thick. The unbroken band signifies that the service is sterile. The banding material 52 remains intact until after the specimen has been collected. The band 52 is cut or broken by the practitioner and one device is then used for a rapid test and the second identical device is sent offsite to be cultured. In another embodiment, the bristles may be impregnated with Strep A antibodies. In this embodiment, a similarly shaped test tube is impregnated with the Strep A antibodies When the bristles is inserted into the test tube, the bristles change color when the Strep A antigen is present. In another embodiment, the test tube may contain a test trip which contains the Strep A antigen, such that when the bristles come in contact with test trip the test strip changes color to signify that the Strep A bacteria is present in the saliva sample. In another embodiment, the circular substance may contain the Strep A antigen, such that when the saliva sample comes in contact with the bristles and travels to the circular substance, the circular substance changes color if the Strep A bacteria is present in the saliva. In another embodiment, the bristle may be 4/16 inches in diameter.

Figure 6:
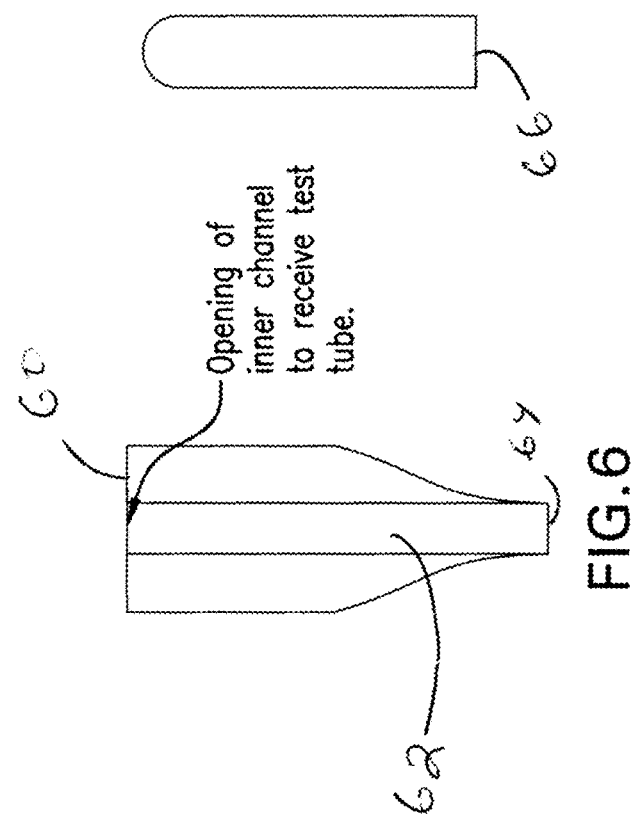
FIG. 6 is a schematic illustration of an alternative embodiment of a device for the detection of Strep A.

In FIG. 6, a multi-component device is shown. The device includes a soft rubber or hard plastic mouthpiece 60. Practitioners may choose which material is the most cost-effective vehicle to be used. The mouthpiece 60 measures 1" wide by 6/16" deep by 2½" long. The mouthpiece 60 has a hollow inner channel 62 which measures 5/16$^{th}$ in diameter and 2½" long. The base of the inner channel has one opening 64. The second component is a plastic test tube 66 which measures 7/16$^{th}$" in diameter and is 2" in length. The test tube 66 is removed from a sterile package by a practitioner and inserted into the hollow channel on the bottom of the mouthpiece. The child coughs into the mouthpiece 60, and the streptococci bacteria sample travels through the inner channel 62 into the test tube 64 where the sample is collected. The test tube 64 is removed from the inner channel of the mouthpiece and placed into a stand. Normal reagents are added directly to the test tube and the rapid test is performed. If the result of the rapid test is negative, a second test tube (not shown) may be attached to the channel of the mouthpiece, and the test is repeated. The second test tube is swabbed with a rayon swab, to collect the bacteria produced by the cough, and is sent off site to be cultured. In another embodiment, the test tube is impregnated with the Strep A antibodies, such that when the bristles are inserted into the test tube, the bristles change color when the Strep A antigen is present. In another embodiment, the test tube may contain a test trip which contains the Strep A antigen, such that the test trip turns colors if the Strep A bacteria is present in in the saliva of the individual.

In another embodiment, a colored fiber membrane is attached to the bottom of the mouthpiece, which would be impregnated with Strep A antibodies. The child then coughs into the mouthpiece, and saliva produced by the cough is collected on the fiber membrane. The fiber membrane would change to a different color if the Strep A antigen is detected in the saliva.

The following sources are hereby incorporated by reference:

Bisno Al Group A Streptococcal Infections and acute rheumatic fever. New England Journal of Medicine 325:783-793 (1991)

Kuttner AGand KrumweideE. Observations on the effect of streptococcal upper respiratory infections on rheumatic children: a three-year study. Clin. Invest.:273-287 (1941)

Shea, Y. Specimen Collection and Transport in Clinical Microbiology Handbook. Isenberg H. D. Am Society of Microbiology 1.1 1-11.30 (1992)

Polymedco Inc. Poly Stat Strep A Strip Test leaflet

CDC Website specifically information on Strep A bacteria (2011)

UCSF Medical Center Clinical Laboratories Point of Care testing (White Paper) Approved by Tim Hammil, MD Quidel Corporation's CEO Presents at The JP Morgan Healthcare Conference (Transcript) Jan. 11, 2012

The methods and systems of the disclosed embodiments, as described above and shown in the drawings, provide for equipment and related techniques with superior attributes including, among other things, improved ease of use. It will be apparent to those skilled in the art that various modifications and variations may be made in the devices and methods of the disclosed embodiments without departing from the spirit or scope of the disclosure. Thus, it is intended that the disclosure include modifications and variations that are within the scope of the appended claims and their equivalents.

What is claimed is:

1. A device for rapidly detecting streptococcus bacteria, including:
   a) a first elongate handle having a proximal end and a distal end, the distal end of the first handle being connected to a first edible substance; and
   b) a second elongate handle having a proximal end and a distal end, the distal end of the second handle being connected to a second edible substance;
   c) the first elongate handle being connected to and maintained in contact along at least a portion of its longitudinal length with the second elongate handle by a banding material; and d) the first edible substance and the second edible substance being configured to be inserted into the mouth of an individual for receiving a saliva sample.

2. The device of claim 1 wherein the first and second edible substances include a plurality of edible components selected from the group consisting of corn syrup, sugar, water, gelatin, modified corn syrup, and mineral oil.

3. The device of claim 1, wherein the first and second elongate handles include at least one of plastic and wood.

4. The device of claim 1, wherein the banding material includes glue or tape.

5. A device for rapidly detecting streptococcus bacteria, including:
   a) an outer elongate tubular handle having a proximal end and a distal end, the distal end of the outer elongate tubular handle being disposed within an edible substance; and
   b) a plurality of swabs for receiving a saliva sample slidably disposed so as to be extendable and retractable within a range of longitudinal positions with respect to an elongate passage of the outer elongate tubular handle, the plurality of swabs being slidable out of a distal end of the edible substance to receive the saliva sample.

6. The device of claim 5, further comprising an elongate proximal handle disposed within the elongate passage of the outer elongate tubular handle, the elongate proximal handle being disposed in operable communication with the plurality of swabs to advance the plurality of swabs into a throat of a patient after the edible material is disposed in the mouth of the patient.

7. A device for rapidly detecting streptococcus bacteria, including:
   a) an outer elongate flavored tubular handle having a proximal end and a distal end; and
   b) a plurality of swabs slidably disposed so as to be extendable and retractable within a range of longitudinal positions with respect to and within the outer elongate flavored tubular handle, each swab being mounted on a respective elongate member, ends of the plurality of swab, the plurality of swabs being slidable out of a distal end of the tubular handle to receive the saliva sample.

8. The device of claim 7, further comprising an elongate proximal handle disposed within the elongate passage of the outer elongate tubular handle, the elongate proximal handle being disposed in operable communication with the plurality of swabs to advance the plurality of swabs into a throat of a patient after the edible material is disposed in the mouth of the patient.

9. The device of claim 7, wherein the outer elongate tubular handle includes edible flavored material.

10. A method for rapidly detecting streptococcus bacteria, comprising:
    a) inserting a first elongate handle connected to a first edible substance and a second elongate handle connected to a second edible substance into the mouth of an individual for a predetermined amount of time until saliva is received on the first and second edible substances;
    b) removing a banding material that connects the first elongate handle from the second elongate handle; and
    c) testing the first and second edible substances for strep A bacteria.

* * * * *